United States Patent [19]

Pigiet

[11] Patent Number: 4,738,841

[45] Date of Patent: Apr. 19, 1988

[54] USE OF THIOREDOXIN, THIOREDOXIN-DERIVED, OR THIOREDOXIN-LIKE DITHIOL PEPTIDES IN HAIR CARE PREPARATIONS

[75] Inventor: Vincent P. Pigiet, Winchester, Mass.

[73] Assignee: Repligen Corporation, Cambridge, Mass.

[21] Appl. No.: 899,707

[22] Filed: Aug. 25, 1986

Related U.S. Application Data

[60] Division of Ser. No. 770,498, Aug. 28, 1985, which is a continuation-in-part of Ser. No. 674,893, Nov. 26, 1984, abandoned.

[51] Int. Cl.$^4$ .................... A61K 7/06; A61K 7/09; A61K 7/11; A61K 7/15
[52] U.S. Cl. ................................ 424/70; 424/71; 424/72; 424/73
[58] Field of Search .................. 424/70, 73, 71, 72

[56] References Cited

FOREIGN PATENT DOCUMENTS 0083095 7/1983 European Pat. Off.
56-103106 8/1981 Japan.

OTHER PUBLICATIONS

Holmgren, *Trends in Biochem. Sci.*, "Thioredoxin: Structure & Functions", 6, pp. 26–29 (1981).

*Primary Examiner*—Jerome D. Goldberg
*Assistant Examiner*—F. Krosnick
*Attorney, Agent, or Firm*—Roman Saliwanchik; David R. Saliwanchik

[57] ABSTRACT

The subject invention enables a more efficient management of hair by providing a novel preparation for waving, straightening, softening, or removing hair, employing as a key ingredient the compound thioredoxin or a thioredoxin-derived, or thioredoxin-like, dithiol peptide in combination with thioglycolic acid compounds. This invention allows hair to be treated at a lower pH to minimize hair damage when waving, straightening, or softening the hair; when used to remove hair, objectionable odors of commercial depilatories are minimized or eliminated.

1 Claim, No Drawings

USE OF THIOREDOXIN, THIOREDOXIN-DERIVED, OR THIOREDOXIN-LIKE DITHIOL PEPTIDES IN HAIR CARE PREPARATIONS

CROSS REFERENCE TO A RELATED APPLICATION

The present application is a divisional application of co-pending application Ser. No. 770,498 filed Aug. 28, 1985 which is a continuation-in-part of Ser. No. 674,893 filed Nov. 26, 1984 now abandoned.

BACKGROUND OF THE INVENTION

The care of hair has been of utmost importance to mankind from the beginning of recorded history. The reign of Queen Elizabeth (1558-1603) became noted for its attention to the finer aspects of hair styling: it was Her Majesty who set the standard. During this Elizabethan period, hair was arranged in elaborate high coiffures, and curled and frizzed by whatever means were available. Needless to say, as measured by present day available hair care products and methods, the Elizabethan hair care procedures were primitive, at best. The discovery of new chemicals and properties thereof led to the beginning of hair careproducts designed to beautify and maintain the hair in a healthy, youthful state. These desirable human hair properties were achieved by use of a variety of hair care products, including hair dyes and products used to impart a wave to the hair. Wavy hair is considered a desirable human hair feature, whereas straight hair is generally held in less favor. Because of these human demands to beautify the hair, there has evolved a multitude of hair care products with a variety of claims and promises. With hair care products designed to dye or wave the hair, it has been found that the structure of the hair shaft itself must be reckoned with in order to have a product which would give the desired results. A key detail of the hair shaft, which is predominantly keratinaceous in nature, is that the keratin fibers are bonded together by disulfide cross-linkages. It is this detail of the hair structure which the subject invention is concerned with. The prior art discloses the severance of the disulfide crosslink with, enter alia, various chemical agents. Perhaps the most widely used chemical, which is referred to as a reducing agent since the disulfide crosslink is converted to sulfhydryl groups, is thioglycolic acid. Use of other mercaptans, or thiols, have been tried but thioglycolic acid or salts thereof appear to be the agent of choice in commercial hair waving products. Recognized limitations of these current thioglycolate-based waving formulations include their sensitivity to air oxidation, their inherent unpleasant odor, and their marginal efficacy at neutral pH. The general requirement for highly alkaline conditions ($\geq$PH 8.5) combined with high thiol concentration is jointly responsible for hair damage described as "overprocessing."

BRIEF SUMMARY OF THE INVENTION

The subject invention concerns the surprising and advantageous discovery that the use of thioglycolic acid and salts thereof (referred to collectively as thioglycolic acid compounds) in hair care preparations can be dramatically improved upon by use of thioredoxin or a thioredoxin-derived, or thioredoxin-like, dithiol peptide in combination with thioglycolic acid compounds. This combination gives rise to a synergistic effect in terms of efficiently breaking the disulfide bond of hair keratin. The net result is that significantly lesser amounts of thioglycolic acid compound are needed to produce the desired effect in the hair. Coupled with this reduction of thioglycolic acid compound use are other desirable features: The hair can be treated at a lower pH to minimize hair damage, and objectionable odors are minimized or eliminated. In achieving these desirable results, the subject invention enhances rather than compromises the reductive properties of thioglycolic acid compounds and additive dithiol peptides.

DETAILED DISCLOSURE OF THE INVENTION

Upon adding thioredoxin or a thioredoxin-derived, or thioredoxin-like, dithiol peptide to a hair care product containing a thioglycolic acid compound, e.g., a preparation for straightening, waving, removing, or softening hair, there is realized a synergistic effect whereby significantly lesser amounts of thioglycolic acid compound are needed to produce the desired effect. For example, in commercial practice thioglycolic acid (TGA) is used in waving lotions at about a 0.6M (Molar) concentration. As the TGA concentration increases from about 0.01 to about 0.6M, the amount of hair curling increases, with a leveling off occurring at about 0.4M TGA. By adding thioredoxin or a thioredoxin-derived, or thioredoxin-like, dithiol peptide to the waving preparation, the TGA concentration can be reduced by a factor of 4 (to about 0.15M) and still give the same amount of waving as a commercial waving lotion containing 0.6M TGA.

The concentration of thioredoxin or one of the thioredoxin-derived, or thioredoxin-like, dithiol peptides which can be used to enhance the effect of a TGA compound ranges from about 1 to about 100 nmole/ml. The optimal concentration for intact bacterial thioredoxin appears to be about 2 nmole/ml. It should be recognized that the precise level of thioredoxin or thioredoxin-derived, or thioredoxin-like, dithiol peptide in combination with TGA compound can be readily ascertained for a particular hair sample by a person skilled in the hair care art having possession of the subject invention.

Thioredoxins are low molecular weight dithiol proteins that have the ability to reduce disulfides in typical organic compounds such as Elman's reagent or disulfides as they exist naturally in a variety of proteins (Holmgren, A. [1981] Trends in Biochemical Science, 6, 26–39).

Thioredoxin and thioredoxin-derived, or thioredoxin-like, dithiol peptides within the scope of the subject invention are exemplified by the following compounds:

(1) thioredoxin isolated from *Escherichia coli* (Laurent, T. C., Moore, E. C., and Reichard, P. [1964] J. Biol. Chem., 239, 3436–3445);

(2) thioredoxins isolated from other sources, e.g., thioredoxin isolated from yeast (Porque, G. P., Baldesten, A., and Reichard, P. [1970] J. Biol. Chem., 245, 2362–2379); *Cyanobacterium* (Gleason, F. K. and Holmgren, A. [1983] in "Thioredoxins, Structure and Function" [P. Gadal, ed.] Editions du Centre National de la Recherche Scientifique); rat (Guerara, J., Moore, E. C., and Ward, D.NM. [1983] ibid: T$_4$ bacteriophage (Soderberg, B-O, Sjoberg, B-M, Sonnerstam, U., and Branden, C-I [1978] Proc. Natl. Acad. Sci. USA, 75, 5827–5830):

(3) thioredoxin-derived dithiol peptides representing peptides produced by cleavage of intact thioredoxins, as described in Example 2, infra. One such example of this class of thioredoxinderived peptides is the fragment containing residues 1 through 37 (i.e., $T_{1-37}$) produced by cyanogen bromide cleavage of thioredoxin from *E. coli*. An important feature of these thioredoxin-derived dithiol peptides is that they contain the redox-active peptide sequence, Cys-X-Y-Cys-Lys, wherein X and Y, independently, can be any of the 20 amino acids. For example, the redox-active peptide sequence from *E. coli* thioredoxin is Cys-Gly-Pro-Cys-Lys (Cys=cysteine, Gly=glycine, Pro-proline, Lys=lysine): and (4) thioredoxin-like dithiol peptides that have the intrinsic ability to catalyze the reduction of protein disulfides. These thioredoxin-like dithiol peptides will generally have the characteristic of containing a pair of cysteine residues which form a redox-active disulfide. This example includes peptides, derived from natural sources or constructed synthetically, that include the same sequence as in *E. coli* thioredoxin, Cys-Gly-Pro-Cys-Lys, or analogous sequences from other thioredoxins such as that encoded for by T4 bacteriophage, Cys-Val-Tyr-Cys (Cys=cysteine, Val=valine, Tyr=tyrosine) (Soderberg, B-O Sjoberg, B-M, Sonnerstam, U., and Branden, C-I [1978] Proc. Natl. Acad. Sci. USA, 75:5827–5830). Other thioredoxinlike peptides include the class of seed proteins called purothionins that have intrinsic thioredoxin-like activity (Wada, K. and Buchanan, B. B. [1983] in "Thioredoxins, Structure and Function" [Gadal, P., ed], Editions du Centre National de la Recherche Scientifique).

Following are examples which illustrate products of the invention and procedures, including the best mode, for practicing the invention. These examples should not be construed as limiting. All percentages are by weight and all solvent mixture proportions are by volume unless otherwise noted.

EXAMPLE 1

Permanent Waving of Hair (a) Commercial Hair Waving Lotion and TGA

Many commercial waving lotions contain as the active ingredient thioglycolic acid. Toni Silkwave TM (for normal hair) (Trademark of Gillette, Boston, Mass. containing waving lotion, neutralizer and shine treatment ingredients) is one such preparation and was used as a reference. A solution of 0.6M sodium thioglycolate, 0.6M ammonium bicarbonate, pH 8.6, was also used as a control for all experiments. Table I shows that the 0.6M TGA solution gave results comparable to the commercial preparation.

TABLE I

Permanent Waving with
TONI SILKWAVE TM and 0.6 M Thioglycolic Acid

| Waving Lotion | Relative Hair Length[1] |
|---|---|
| Toni TM | 0.80 |
| 0.6 M TGA | 0.79 |

[1]Relative Hair Length was determined as follows: Hair tresses were divided into smaller tresses approximately 1 cm wide.

Hair tresses were divided into smaller tresses approximately 1 cm wide.

Each tress was treated with 2 ml of waving lotion. Half of the waving lotion (1 ml) was applied to the tress and combed through. An end paper was folded around the tress to assure that the tress was flat and that all ends were covered. The tress was rolled firmly and evenly on the smallest rods available in the TONI SPIN CURLER TM assortment. After the tress was rolled the remaining waving lotion was applied and the tress kept for 15 minutes at room temperature. After 15 minutes the tress was rinsed for 30 seconds under warm running tap water, blotted dry, and maintained at room temperature for an additional 30 minutes.

The tress was neutralized by applying 2 ml of hydrogen peroxide (0.5%). After 3 minutes the curling rod was removed and an additional 2 ml of hydrogen peroxide was applied. The tress was rinsed for 30 seconds under warm running tap water, blotted dry, and allowed to completely air-dry before making any measurements.

Differences in the amount of waving from the different solutions were quantitated by measuring the hanging length before and after waving. The relative hair length was calculated as shown in the following equation:

$$RHL = \frac{L_a}{L_b}$$

where RHL is the relative hair length, $L_b$ the length before waving, and $L_a$ the length after waving.

(b) Influence of TGA

TGA concentration ranging from about 0.01 to about 0.6M was evaluated in a solution containing ammonium bicarbonate ($NH_4HCO_3$) in the same molar concentration as TGA at pH 8.6. The influence on waving was determined in the absence and presence of 10 nmole/ml of thioredoxin. Two hair lots were also used. The tresses were waved and the relative hair length determined as described above. The results showed that as the TGA concentration increased from about 0.01 to about 0.6M the amount of curling also increased and leveled off at approximately 0.4M.

In the presence of thioredoxin (10 nmole/ml) there was an increase in the amount of waving measured at each concentration of TGA used. At higher TGA concentrations this effect was more pronounced and could be easily visualized. At 0.2M TGA the amount of waving in the presence of thioredoxin was greater than that of either 0.6M TGA alone or the Toni TM waving lotion. With thioredoxin present the TGA concentration could be reduced by a factor of 4 (to 0.15M) and still give the same amount of waving as the commercial waving lotion.

(c) Influence of Thioredoxin

The influence of thioredoxin on permanent hair waving at various TGA concentrations was tested with thioredoxin concentrations ranging between about 10 and about 100 nmole/ml. Thioredoxin was added to the waving solution, mixed well, and applied to hair tresses as described above The waving solutions used were: (1) 0.1M TGA, 0.1M $NH_4CO_3$, pH 8.6, (2) 0.2M $NH_4HCO_3$, pH 8.6, and (3) 0.4M TGA, 0.4M $NH_4HCO_3$, pH 8.6. The results showed that a thioredoxin concentration of 10 nmole/ml gave maximal waving.

In a second test, thioredoxin concentrations were varied from about 1 to about 10 nmole/ml. The waving solution was solution (2) above. The results showed that thioredoxin concentration can be decreased to as low as 2 nmole/ml before there is a noticeable decrease in the effect on waving.

(d) Influence of pH

One disadvantage of the commercial permanent waving preparations is the high pH. Thus, an object of the subject invention is to be able to lower the pH and still obtain a high level of waving. When the pH was decreased from 8.5 to 7.5 there was also a decrease in the amount of waving, both in the presence and absence of thioredoxin. At pH 7.5, however, the amount of waving in the presence of thioredoxin and 0.2M TGA was still greater than the amount of waving with the 0.2M TGA alone at pH 8.6. At pH near neutral, TGA becomes a less efficient reducing agent, contributing to the decreased waving, both in the presence and absence of thioredoxin.

The pH was adjusted with concentrated HCl. The waving solutions contained 0.2M TGA and 0.2M NH$_4$HCO$_3$ and 0.2M TGA, 0.2M NH$_4$HCO$_3$, and 40 nmole/ml thioredoxin. The experimental procedure was as described above.

EXAMPLE 2

Influence of Thioredoxin Fragments T$_{1-37}$ and T$_{19-36}$ on Permanent Hair Waving

(a) Production of T$_{1-37}$ by Cyanogen Bromide Cleavage

A sample of *E. coli* thioredoxin was dialyzed in water for 12 hr at 4° C. Five ml was dried and resuspended in 70% formic acid Cyanogen bromide (Sigma Chemical, St Louis, Mo.) was dissolved in 70% formic acid and added to thioredoxin in a 50-fold molar excess of methionine The solution was purged with nitrogen and incubated at room temperature in the dark for 24 hr. At the completion of the cleavage reaction the solution was dried under nitrogen, resuspended in sodium acetate buffer and adjusted to pH 8.5 with ammonium hydroxide.

Samples were loaded onto a Waters μ-Bondapak C-18 column (Trademark of Waters Associates, Inc., Milford, Mass.) attached to a Beckman Model 421 system (Trademark of Beckman Instruments, Inc. Fullerton, Calif.) monitored at 214 nm. The solvent system employed was 0.1% trifluoroacetic acid (Buffer A) and 0.08% trifluoroacetic acid in acetonitrile (Buffer B). A gradient from 0% to 60% B over 30 min was used to separate the oeotides at a flow rate of 2 ml/min.

Thioredoxin was cleaved by CNBr into two fragments, T$_{1-37}$ and T$_{38-108}$, eluting at 44% and 51% buffer B, respectively. Amino acid analysis identified and confirmed the composition of both peptides. (Holmgren, A. and Reichard, P. [1967] Eur. J. Biochem. 2, 187–196). T$_{1-37}$ contained the active site of the enzyme. The two peptides recovered accounted for 69% of the starting material. Unreacted thioredoxin accounted for 12–15% of the loss, while HPLC separation may be responsible for the additional losses.

(b) Production of T$_{19-36}$ by Trypsin Cleavage

After HPLC separation, described above, T$_{1-37}$ was pooled, dried, and resuspended in sodium acetate buffer and adjusted to pH 8.0 with NH$_4$OH. An aliquot of trypsin (Sigma Chemical) was added to the incubation at 1% (w/w) of peptide concentration. The reaction mixture was incubated at 37° C. for 1 hr. Separation of trypsin fragments was done by HPLC as for the cyanogen bromide fragments.

Trypsin digestion of the T$_{1-37}$ peptide yielded two peptides, T$_{4-18}$ and T$_{19-36}$, which were resolved by HPLC, eluting at 31% and 45% in buffer B, respectively. Amino acid analysis revealed that the species eluting at 31% B contained 15 amino acids and corresponds to the active site peptide, T$_{19-36}$. Incubation of 90 nmoles of T$_{1-37}$ produced 80 nmoles T$_{19-36}$ after separation by HPLC with a yield of 88%.

Residues 19 through 36 can be used in the same manner as residues 1–37, described herein.

(c) Influence of Fragment T$_{1-37}$ on Permanent Hair Waving

The effect of T$_{1-37}$ peptide on waving is shown in Table II. The peptide has a comparable influence on waving as the intact thioredoxin. In this study the concentration used was twice as great as that of the intact thioredoxin. In a second test, T$_{1-37}$ peptide was varied from about 1 to about 80 nmoles/ml. The waving solution is the same as described in Table II. The results showed that the T$_{1-37}$ peptide can be decreased to as low as 1 nmole/ml before there is any noticeable decrease in the effect on waving.

TABLE II

| Influence of Fragment T$_{1-37}$ on Permanent Hair Waving | | |
|---|---|---|
| | Relative Hair Length | |
| Waving Lotion | A | B |
| 0.2 M TGA | 0.84 | 0.81 |
| 0.2 M TGA + Thioredoxin[1] | 0.79 | 0.73 |
| 0.2 M TGA + T$_{1-37}$[2] | 0.79 | 0.73 |

[1]The thioredoxin concentration in both A and B was 10 nmole/ml.
[2]The T$_{1-37}$ fragment concentration was 26 nmole/ml for A and 20 nmole/ml for B.
A and B were run on two different days using two different lots of hair. The pH for all assays was 8.6.

EXAMPLE 3

Production of Purified Thioredoxin

Thioredoxin is purified either from a commercial source of *E. coli*, strain B (Grain Processing Corp., Minneapolis, Minn.) or from any of a number of common strains of *E. coli* grown by a standard procedures (Pigiet, V. and Conley, R. R. [1977] J. Biol. Chem., 252, 6367–6372). The protein is purified using standard procedures including chromatography on ion exchange and molecular seive columns (Williams, C. H., Zanetti, G., Arscott, L. D., and McAllister, J. K. [1967] J. Biol. Chem., 242, 5226–5231; McEvoy, M., Lantz, C., Lunn, C. A., and Pigiet, V. [1981] J. Biol. Chem., 256, 6646–6650).

Thioredoxin protein is assayed immunologically using quantitative rocket immunoelectrophoresis as described in McEvoy et al., supra.

EXAMPLE 4

Hair Straightening

The following formula, or obvious variations thereof, incorporating thioredoxin or a thioredoxin-derived, or thioredoxin-like, dithiol peptide, can be used with known procedures to straighten hair:

| | per cent |
|---|---|
| Emulsion base: | |
| Demineralized water | to 100.0 |
| Cetyl alcohol emulsified by oxyethylated cetyl alcohol | 22.0 |
| Demineralized water | 30.0 |
| Sodium carbonate glycinate | 5.0 |
| Ammomium thioglycollate or thiolactate (50% aqueous soln) | 3.0 |
| EDTA (disodium salt) | 0.3 |
| Sodium p-hydroxybenzoate methyl ester | 0.05 |
| Monoethanolamine | 2.0 |
| Imidazoline | 0.2 |
| Perfume | 0.2 |
| Thioredoxin or a thioredoxin-derived, or thioredoxin-like, dithiol peptide | 1–100 nmole/ml |

EXAMPLE 5

Hair Removal

The following formula, or obvious variations thereof, incorporating thioredoxin or a thioredoxin-derived, or thioredoxin-like, dithiol peptide, can be used with known procedures to remove hair;

| | percent |
|---|---|
| Sodium picosulfate | 6.5 |
| Calcium thioglycollate | 1.5 |
| Calcium hydroxide | 7.0 |
| Sodium lauryl sulfate | 0.02 |
| Sodium silicate 'O' | 3.43 |
| Thioredoxin or a thioredoxin-derived, or thioredoxin-like, dithiol peptide | 1–100 nmole/ml |
| Perfume | q.s. |
| Distilled water | to 100.0 |

Procedure: Heat the water to 70° C. With stirring add the sodium lauryl sulfate and sodium picosulfate; continue stirring until melted and dispersed. Discontinue heating and cool/stir to room temperature. Add the calcium hydroxide and perfume. Add the calcium thioglycollate and thioredoxin or a thioredoxin derived, or thioredoxin-like, dithiol peptide and stir until uniform.

EXAMPLE 6

Hair Softening

Thioredoxin or a thioredoxin-derived, or thioredoxin-like, dithiol peptide can be incorporated, advantageously, into a standard lather shaving cream or brushless shaving cream to soften the hair. This softening of the hair compliments the softening realized by the soap and water contact with such shaving creams. The level of thioredoxin or a thioredoxin-derived, or thioredoxin-like, dithiol peptide used in such shaving creams can be varied as described above. Likewise, the percentage of soaps of such standard shaving creams can be reduced with the use of the compounds of the invention. The particular levels of soap, thioglycolic acid compound, and thioredoxin or a thioredoxin-derived, or thioredoxin-like, dithiol peptide can be adjusted readily by a person skilled in the art to meet the requirements for softening different types of hair.

EXAMPLE 7

Animal Hair

The compositions and porcesses of the previous examples can be readily adapted by a person skilled in the art to be used to care for animal hair in general, e.g., dog, cat, horse, and the like.

I claim:

1. A process for softening human or animal hair which comprises applying to said human or animal hair a composition comprising a thioglycolic acid compound at a concentration of about 0.01M to about 0.2M, and a thioredoxin or thioredoxin-derived, or thioredoxin-like, dithiol peptide at a concentration of about 1 nmole/ml to about 100 nmole/ml.

* * * * *

UNITED STATES PATENT AND TRADEMARK OFFICE
CERTIFICATE OF CORRECTION

PATENT NO. : 4,738,841
DATED : April 19, 1988
INVENTOR(S) : Vincent P. Pigiet

It is certified that error appears in the above-identified patent and that said Letters Patent are hereby corrected as shown below:

Column 3: line 49: "Toni Silkwave$^{TM}$" should read --TONI SILKWAVE$^{TM}$--.

Column 5: line 34: after "formic acid" insert --.--; line 37: after "onine" insert --.--; line 51: "oeotides" should read --peptides--.

Column 7: line 4: "Emulsion base:" should read --Emulsion base:--; line 5: "Demineralized water" should be indented; line 6: "Cetyl alcohol emulsified" should be indented; line 7: "by oxyethylated cetyl alcohol" should be indented.

Column 8: line 28: "porcesses" should read --processes--.

Signed and Sealed this

Thirtieth Day of August, 1988

Attest:

DONALD J. QUIGG

Attesting Officer

Commissioner of Patents and Trademarks